US00PP18110P3

(12) United States Plant Patent
Randag

(10) Patent No.: US PP18,110 P3
(45) Date of Patent: Oct. 9, 2007

(54) VARIETY OF CALLA LILY NAMED 'MAJESTIC STAR'

(50) Latin Name: *Zantedeschia sprengeri*
Varietal Denomination: Majestic Star

(75) Inventor: Cecilius Jan-Jochem Randag, CJ 't Zand (NL)

(73) Assignee: Sande B.V. (NL)

( * ) Notice: Subject to any disclaimer, the term of this patent is extended or adjusted under 35 U.S.C. 154(b) by 249 days.

(21) Appl. No.: 11/200,737

(22) Filed: Aug. 10, 2005

(65) Prior Publication Data

US 2007/0039082 P1 Feb. 15, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—The Webb Law Firm

(57) ABSTRACT

'Majestic Star' is a new variety of calla lily having an inflorescence with a deep red colored spathe and a yellow colored spadix and producing 1–6 inflorescences per tuber. The inflorescence stems are red and about 60 cm. in height. The leaves are green with whitish spots and have a leathery texture. On the edge of the leaves there is a red stripe. The petioles have a purple red color.

4 Drawing Sheets

Botanical classification: *Zantedeschia sprengeri.*
Varietal denomination: 'Majestic Star'.

BACKGROUND OF THE NEW PLANT

The present invention comprises a new and distinct cultivar of calla lily, botanically known as *Zantedeschia sprengeri* and hereinafter referred to by the cultivar name 'Majestic Star'.

'Majestic Star' is a naturally occurring, whole plant mutation from a planned breeding program which has the objective of creating *Zantedeschia* hybrids for cut flower production in a wide range of colors with a large, classic flower shape. The breeding program began in 1989 and the new cultivar is a mutant selected from a large population of a *Zantedeschia sprengeri* variety known as 'Black Star' (U.S. Plant Pat. No. 14,844). 'Majestic Star' was discovered in 2003 by the inventor C. J. J. Randag in CJ't Zand, The Netherlands, as one flowering plant within the population of 'Black Star'.

The first act of asexual reproduction of 'Majestic Star' by tissue culture was performed by the inventor in September 2003 in CJ't Zand, The Netherlands. Subsequent asexual reproduction by tissue culture at the same location has demonstrated that the combination of characteristics as herein disclosed for the new cultivar are retained and reproduced true to type through successive generations of asexual reproduction.

The following observations, measurements and comparisons describe plants grown in CJ't Zand, The Netherlands under greenhouse conditions which approximate those generally used in horticultural practice. Color references are made to The R.H.S. Colour Chart of The Royal Horticulture Society of London, except where general color terms of ordinary significance are used.

The present invention has not been evaluated under all possible environmental conditions. The phenotype may vary with variation in environment without a change in the genotype of the plant.

The following traits have been observed and determined to basic characteristics of 'Majestic Star' which, in combination, distinguish this calla lily as a new and distinct cultivar:

1. Deep red spathe;
2. Yellow spadix with red spots;
3. Red flower stem;
4. Red edge on the leaves; and
5. Red petiole of the leaves.

BRIEF DESCRIPTION OF THE DRAWINGS

The accompanying photographic drawings illustrate the new variety, with the colors being as nearly true as is possible with color illustrations of this type.

DESCRIPTION OF THE PLANT

Figure 1:
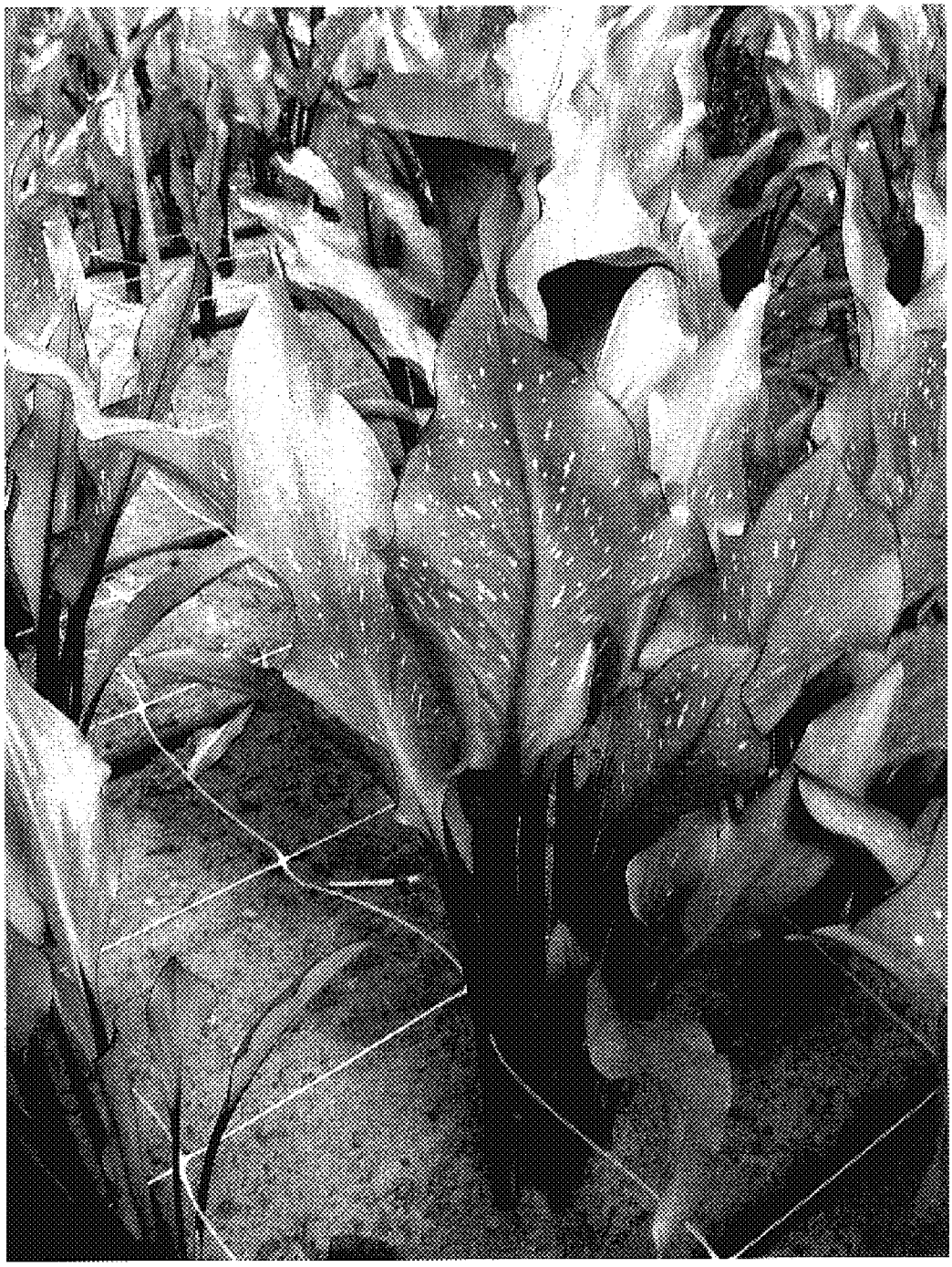
FIG. 1 is a photograph of the whole plant of 'Majestic Star'.
Figure 2:
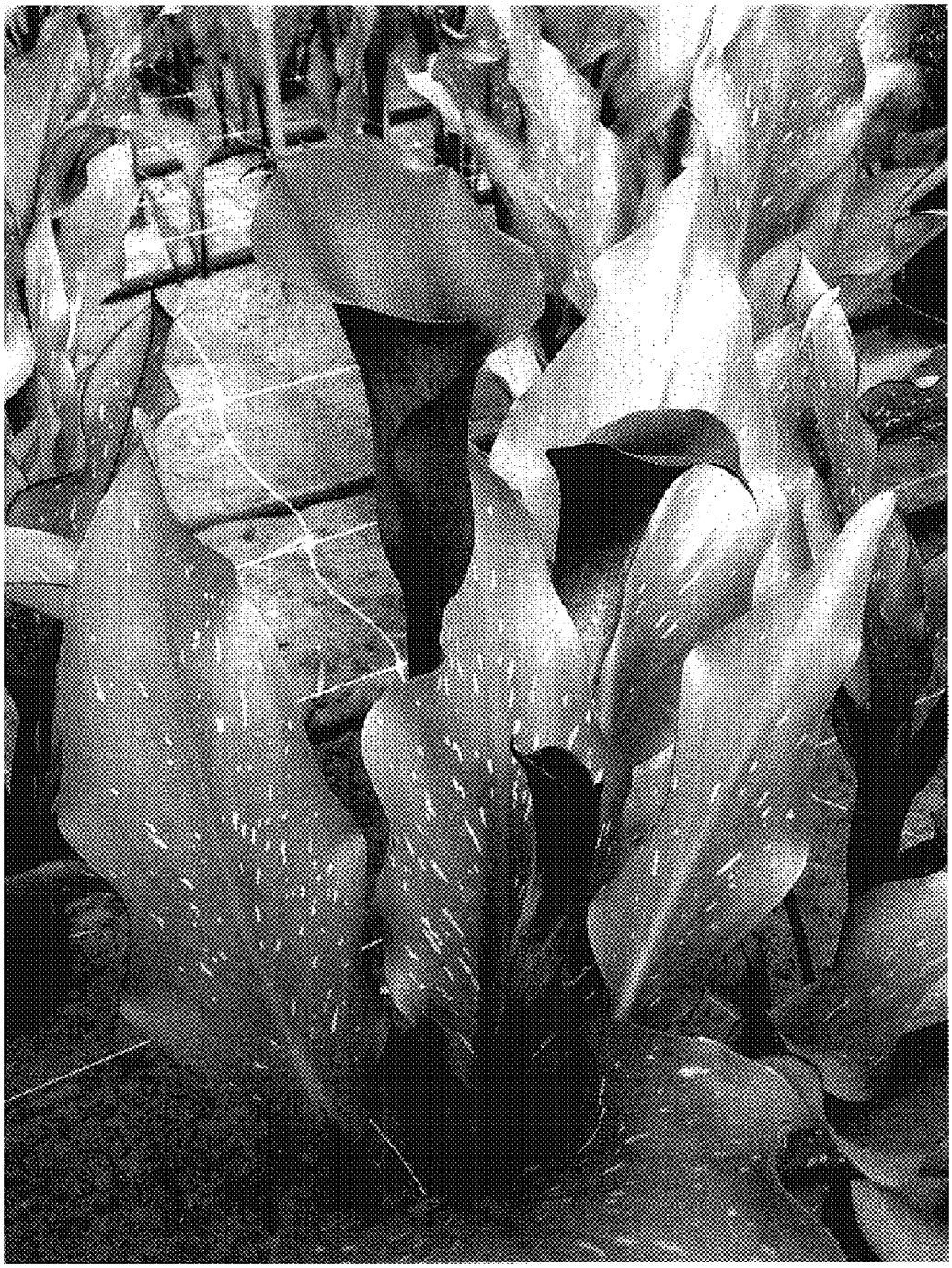
FIG. 2 is a photograph of the spathe on the outside.
Figure 3:
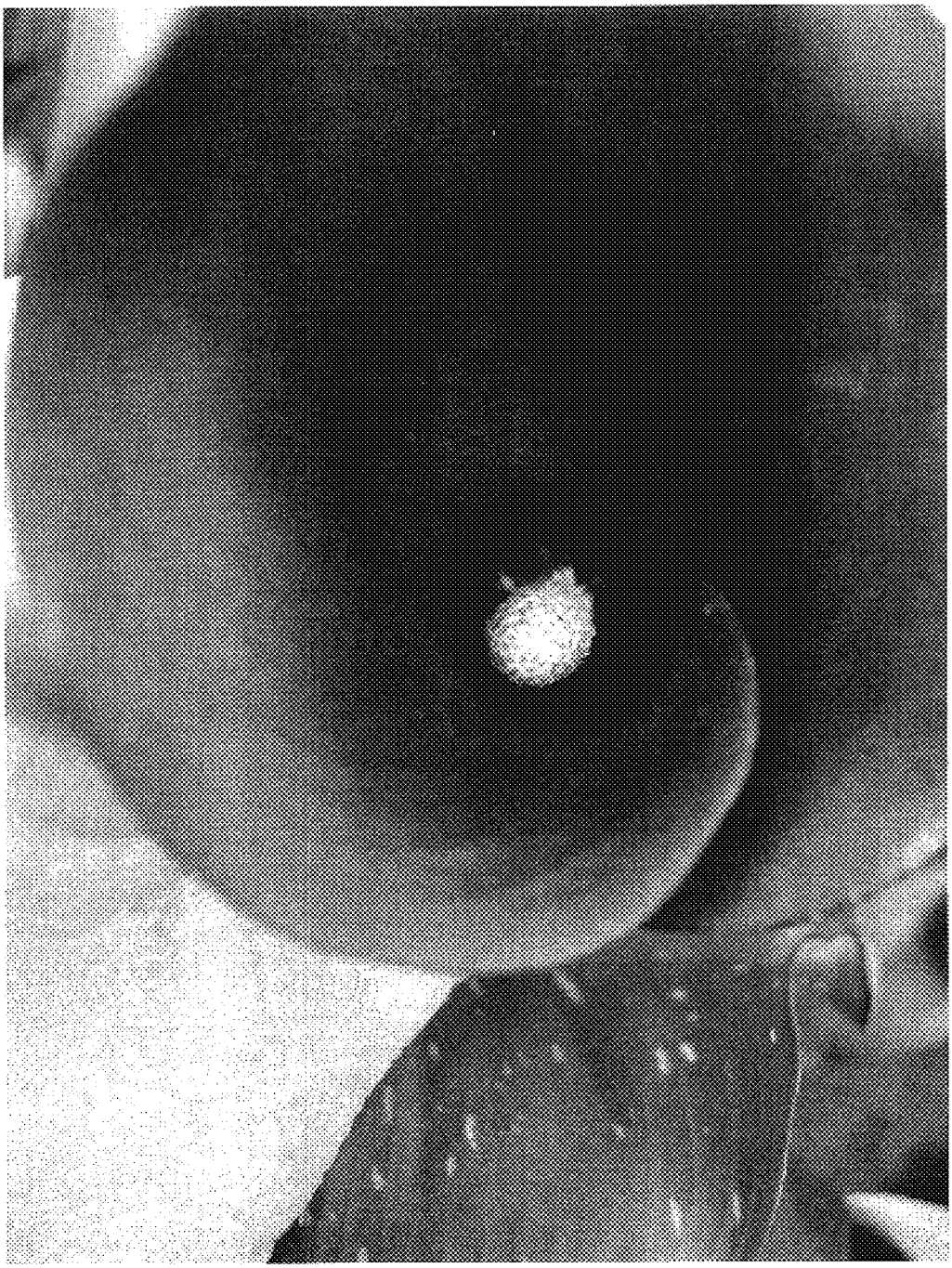
FIG. 3 is a photograph of the inside of the spathe.
Figure 4:
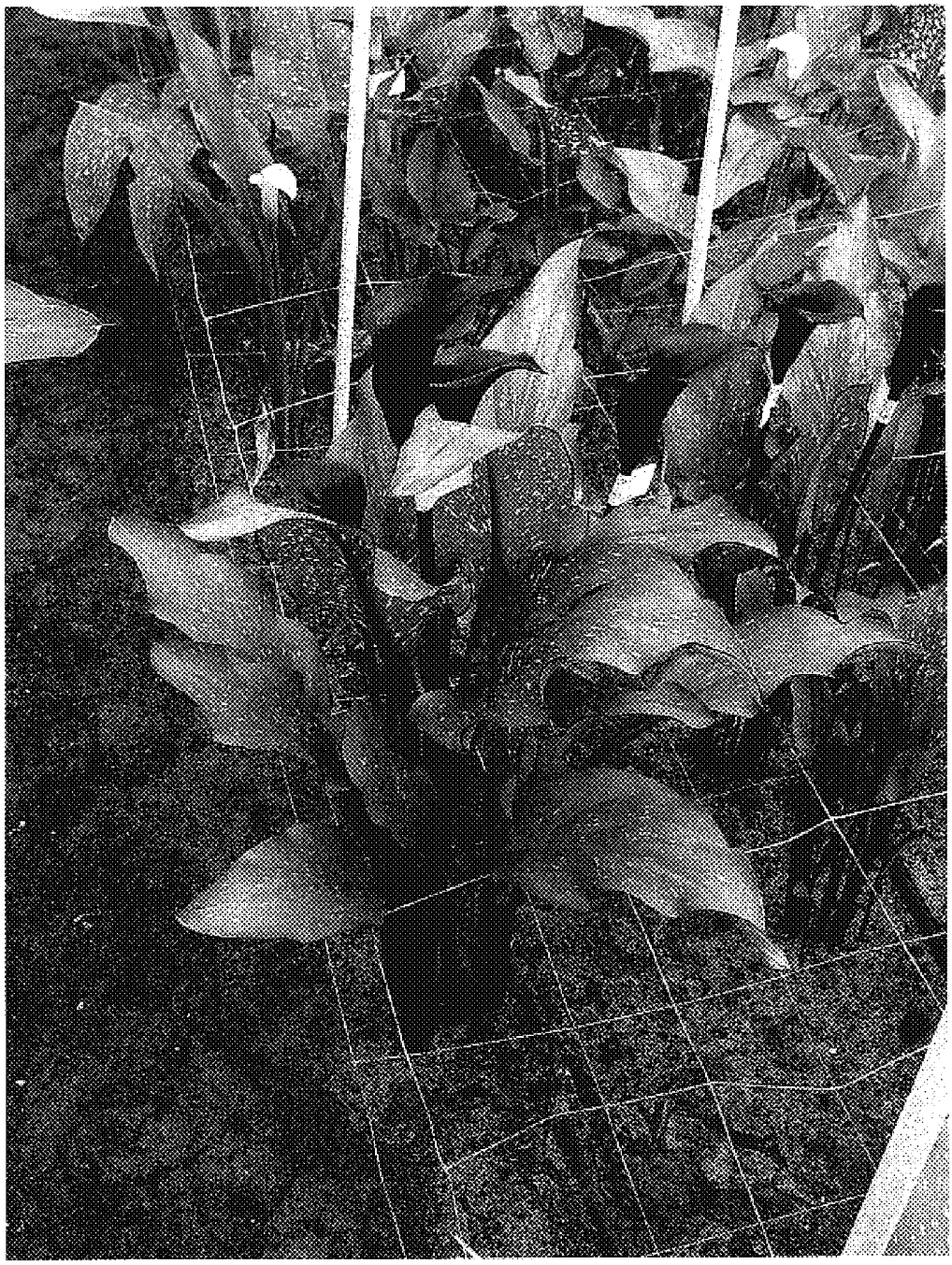
FIG. 4 is a photograph of 'Black Star'.

Size:
*Height of the leaf canopy above the soil.*—45–50 cm.
*Height of top of inflorescence above the soil.*—50–55 cm.
*Diameter.*—12–15 cm.
Form: Erect.
Number of inflorescences per tuber:
*Circumference of 9–12 cm.*—0–1 inflorescences.
*Circumference of 12–14 cm.*—1–3 inflorescences.
*Circumference of 14–16 cm.*—2–4 inflorescences.
*Circumference of 16–18 cm.*—3–5 inflorescences.
*Circumference of 18/+cm.*—5 or more inflorescences.
Average tuber diameter: 4.5 cm.

Branches:
*Character.*—Average.
*Color.*—Between Green Group 141C and Yellow-Green RHS 146B with spots of Red Group RHS 53A. The base is Green-White Group RHS 157C with Red-Purple Group RHS 59A and 59B spots.

Leaves:
*Size.*—Width: 10–12 cm. Length: 23–28 cm.
*Number per plant.*—4–10.
*Shape.*—Elliptic.
*Apex.*—Rostratus.
*Base.*—Angustatus.
*Color.*—Upper surface: Green Group RHS 137B–137C. Lower surface: Yellow-Green RHS 137B–137C.
*Margin.*—Wavy with a Red-Purple Group RHS 59A line.
*Veins.*—Configuration: Pinnate. Color: Yellow-Green Group RHS 144A–53A.
*Surface texture.*—Leathery.
*Petiole.*—Length: 26–31 cm. Color: The base is Red Group RHS 53A and the upper part varies between Red Group RHS 53A–53C.

Roots:
*Color.*—White.
*Branching.*—Comparable with 'Black Star'.

INFLORESCENCE

Spathe:
*Size.*—Length: 7–10 cm. Width: 5–8 cm.
*Color.*—Upper surface: Between Red Group RHS 53A and Red-Purple Group RHS 60A. Lower surface: Between Red-Purple Group RHS 60B and RHS 60C.
*Veins.*—Color: Varies between RHS 60B and RHS 60C.
*Shape.*—Cupped.
*Apex.*—Aristate.
*Base.*—Obtuse.
*Margin.*—Undulate.

Spadix:
*Size.*—Length: 20–45 mm. Diameter: 3–7 mm.
*Color.*—Varies between RHS Yellow-Orange Group 15A and 15B with spots between Red-Purple Group RHS 59A and 60A.
*Position relative to spathe.*—Upright.

Peduncle:
*Size.*—Length: 45–80 cm. Diameter: 8–10 mm.
*Color.*—Varies between Red Group RHS 53B and RHS 53C.

Reproductive organs:
*Location of female organs.*—Basal position of the spadix.
*Location of male organs.*—Upper position of the spadix.
*Perianth.*—Conspicuous.
*Stamens.*—Not visible before pollen release.
*Amount of pollen released.*—On a scale of 1 to 5 where 1 is no pollen released and 5 is heavy pollen released, the new variety is a 2.

Pistal:
*Length beyond perianth.*—About 1 mm.

Disease resistance: None observed.

Pest resistance: None observed.

Flowering: Tubers planted in a greenhouse in The Netherlands in February produce inflorescences in April. Tubers planted outdoors in The Netherlands in May produce inflorescences in July.

Lastingness: About three weeks on the plant and between two to three weeks off the plant.

Fragrance: None.

I claim:

1. A new and distinct variety of calla lily plant named 'Majestic Star' as is herein described and illustrated.

* * * * *